United States Patent
Mitsunaga et al.

(10) Patent No.: US 6,336,003 B1
(45) Date of Patent: Jan. 1, 2002

(54) MAX ONE I.V. WARMER

(75) Inventors: Michael Mitsunaga, Los Angeles; Yoshiaki Yamamoto, Santa Monica, both of CA (US)

(73) Assignee: Automatic Medical Technologies, Inc., Torrance, CA (US)

( * ) Notice: Subject to any disclaimer, the term of this patent is extended or adjusted under 35 U.S.C. 154(b) by 0 days.

(21) Appl. No.: 09/653,692

(22) Filed: Sep. 1, 2000

(51) Int. Cl.$^7$ .............................. A61F 7/00; A61M 5/00
(52) U.S. Cl. .......................................... 392/470; 604/111
(58) Field of Search ........................ 392/470; 604/93.01, 604/111, 113, 118, 151

(56) References Cited

U.S. PATENT DOCUMENTS

| | | | | |
|---|---|---|---|---|
| 4,293,762 A | * | 10/1981 | Ogawa ......................... | 392/470 |
| 4,356,383 A | * | 10/1982 | Dahlberg et al. ............ | 392/470 |
| 4,680,445 A | * | 7/1987 | Ogawa ......................... | 392/470 |
| 4,906,816 A | * | 3/1990 | van Leerdam ............... | 392/470 |
| 5,125,069 A | * | 6/1992 | O'Boyle ...................... | 392/465 |
| 5,381,510 A | * | 1/1995 | Ford et al. ................... | 392/470 |

\* cited by examiner

Primary Examiner—Teresa Walberg
Assistant Examiner—Thor Campbell

(57) ABSTRACT

A reusable heating device comprises a casing to be disposed vertically, the casing including a circuit element receiving chamber and a heater receiving chamber having a front opening, a lid for at least covering the front opening of the heater receiving chamber, a heater situated in the heater receiving chamber, and electric circuit means situated in the circuit element receiving chamber. The heater includes a heater segment coextensive with and disposed in the front opening and an electric heating element attached to a backside and the cover unit of the heater segment. The heater segments have U-shaped channels on a front side thereof to receive therein a Disposable Cellular Pouch through which an instillation liquid to be heated flows. The U-shaped channels include at least left and right curves and extends from an upper portion of the heater segment to a lower portion thereof through the U-shaped channels to keep the instillation liquid in the Disposable Cellular Pouch between the left and right curves for a period sufficient to heat the liquid. The electric circuit means includes first and second temperature control thermistors, the first thermistor sensing temperature of the instillation liquid after passing through the heater segment for intermittently energizing the heater to heat the instillation liquid to a predetermined temperature. The second thermistor is provided at the electric heating element to turn off the electric circuit means when the electric heating element is heated beyond a predetermined temperature due to excessive flow of the instillation liquid to thereby override the control of the heater by the first thermistor. In this case the instillation fluid flow is not halted and will continue to flow without the heating.

3 Claims, 8 Drawing Sheets

DRAWINGS: NOT TO SCALE
TOP VIEW CLOSED UNIT (1) Hanging Band (to I.V. Stand)

(3) Inlet

(14) Closed View of Warmer Unit (4) Outlet (4) 110 Volt Power Source
Hospital Rated U.L.

DRAWINGS: NOT TO SCALE
OPEN VIEW COVER SECTION

Silicon Rubber Heating Pads
(10) 60 Watts
(10) 60 Watts
(11) 30 Watts (9) Cover Plate
(8) Rounded Warming Cchannels
(12) Power Source Distribution
(13) Sliding Lock

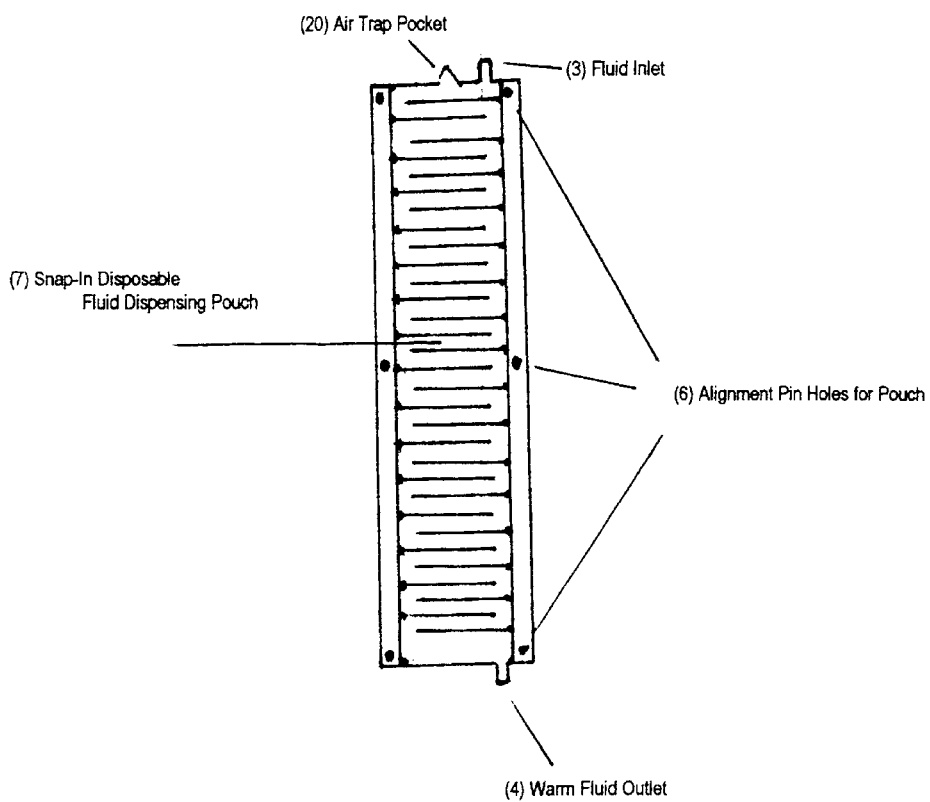

MAX ONE I.V. WARMER

RELATED FIELD

The title of the invention is a reusable Max One I.V. Warmer. The product is a temperature-controlled electric heating device for heating fluid in a Disposable Cellular Pouch for instillation or transfusion I.V. liquids and blood/blood products. The Disposable Cellular Pouch will be offered in various milliliter channel flow sizes for various applications.

BACKGROUND OF THE INVENTION

The present invention relates to a heating device for instillation. More particularly, the invention relates to a heating device for injecting an instillation liquid, a blood/blood products transfusion liquid and or the like into a blood vessel of a patient at an optimum temperature.

According to a conventional technique for heating an instillation liquid or blood/blood products transfusion liquid and injecting the heated liquid into a blood vessel of a patient, a liquid feed pipe is passed through a warm water tank or a warming pad or the fluid is passed through large cumbersome warming units to heat the liquid passing there through up to an appropriate temperature. According to these conventional techniques, it takes time to get ready for instillation. Further, handling or transferring of the heating device is very troublesome.

OBJECTS AND SUMMARY OF THE INVENTION

It is a primary object of the present invention to provide a heating device for instillation, which has a small size, so as not to occupy a large space and to be transferred and handled very easily, and which can improve efficiency of the instillation operation, for example, fast warming, saves time, be a reusable heating unit with a Disposable Cellular Pouch available with various milliliter tubular flow sizes.

Another object of the present invention is to provide a heating device for a Disposable Cellular Pouch for instillation, in which a heater can be effectively utilized for heating an instillation liquid or blood/blood product transfusion liquid. Heat of the heater is transferred to the liquid through U-shaped channels from inlet to outlet on the lid and the main body at a high efficiency without loss of heat so that uneven heating for the instillation liquid or blood/blood products transfusion liquid can be completely prevented.

Still another object of the present invention is to provide a heating device for a Disposable Cellular Pouch for Instillation, in which a liquid feed through which the liquid to be heated flows left and right on a heater to increase contact area between the U-shaped channels and the heater, so that uneven heating can be completely prevented when the instillation liquid or blood/blood products transfusion liquid is heated.

A further object of the present invention is to provide a heating device for a Disposable Cellular Pouch for instillation, in which temperature overshooting of an instillation liquid is prevented during a heating of the instillation liquid by diminishing the thermal capacity of the heater and the instillation liquid can be consistently heated at a predetermined temperature in a short time.

A still further object of the present invention is to provide a heating device for a Disposable Cellular Pouch for instillation, which can be hung at a predetermined position with full view of the temperature and other controls, to be freely adjusted in the vertical direction to be closed to the infusion site, thus eliminating the lost of heat that occurs when a "long line set" is used at the point of infusion.

Other objects of the present invention will be apparent from embodiments described hereinafter and be clarified in appended claims. Various advantages of the present invention will be apparent to those skilled in the Medical arts when the present invention is practically carried out. In accordance with the invention, there is provided a heating device for a Disposable Cellular Pouch for instillation. The heating device comprises a casing to be disposed vertically, the casing including a circuit element receiving chamber and a heater receiving chamber having a front opening, a lid for at least covering the front opening of the heater receiving chamber, a heater situated in the heater receiving chamber, and electric circuit means situated in the circuit element receiving chamber. The heater includes a heater segment disposed in the front opening and an electric heating element attached to a backside of the heater segment. The heater segment have U-shaped channels on a front side thereof to receive therein a Disposable Cellular Pouch through which an instillation liquid to be heated flows. The U-shaped channels includes at least left and right curves and extends from an upper portion of the heater segment to a lower portion thereof through the channels to keep the instillation liquid in the Disposable Cellular Pouch between left and right curves for a time sufficient to heat the liquid. The electric circuit means includes first and second temperature control thermistors, the first thermistor sensing temperature of the instillation liquid after passing through the heater segment for intermittently energizing the heater to heat the instillation liquid to a predetermined temperature. The second thermistor is provided at the electric heating element to turn off the electric circuit means when the electric heating element is heated beyond a predetermined temperature due to excessive flowing of the instillation liquid to thereby override the control of the heater by the first thermistor. This will not stop the flow the fluid, it will continue to flow with the heater off.

The lid includes a pressing member to intimately hold the Disposable Cellular Pouch in the U-shaped channels when the lid is closed. Location pins are provided to hold the Disposable Cellular Pouch between the lid and the pressing member and between the casing and the electric heating element.

The casing and lid are integrally formed of a synthetic resin and are joined by integral hinge so that the lid can be freely opened and closed. A sliding anchoring projection and a hook are provided on the casing and the lid respectively to keep the lid closed.

BRIEF DESCRIPTION OF THE DRAWING

FIG. 8 is a perspective view illustrating embodiment of the Disposable Cellular Pouch. The pouch is designed to hold the fluid long enough to allow the heating units to warm the fluid to the desired temperature. Second, it is disposable once it is used by the Medical Technician and is disposed easily with the other disposable items used by the technicians. The warmer is then ready for use immediately for the next procedure. Various milliliter flow channel size will be available for use in the heating unit that will correspond to the procedure use.

DETAILED DESCRIPTION OF THE PREFERRED EMBODIMENTS

Figure 1:
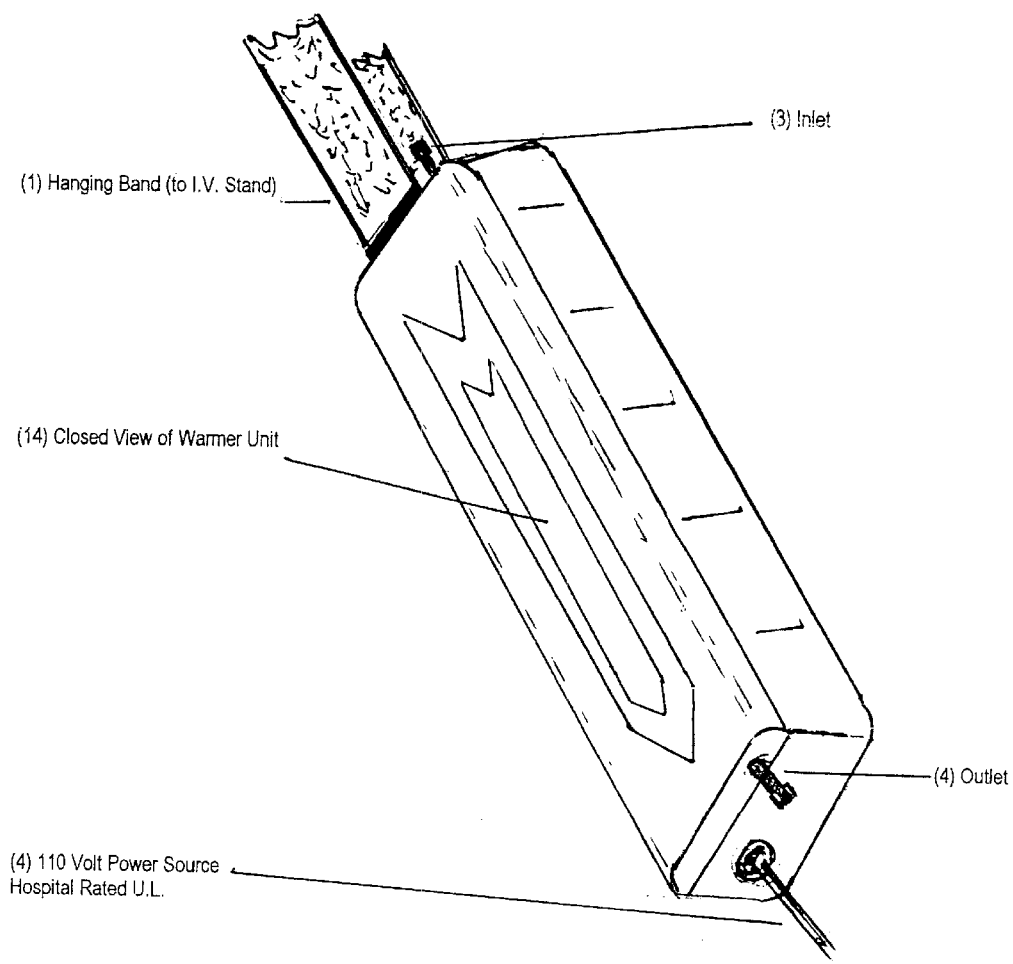
FIG. 1 is a perspective view illustrating one embodiment of the heating device for instillation according to the present invention in which a lid is closed.
Figure 2:
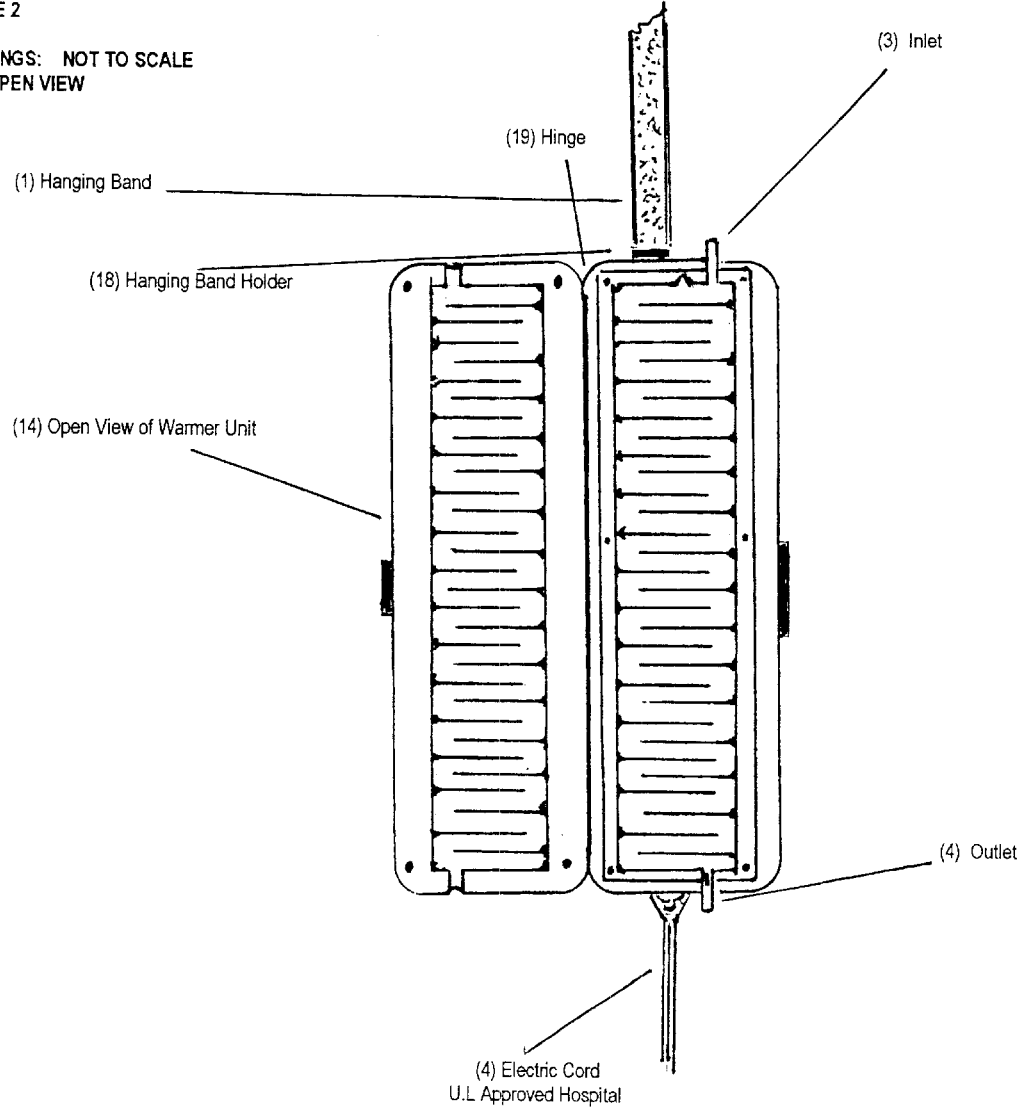
FIG. 2 is a perspective view illustrating one embodiment of the heating device for instillation according to the present invention in which a lid is opened.

Embodiments of the heating device of the present invention will now be described with reference to the accompanying drawings.

The heating device comprises of heater-receiving chambers having a front opening and a circuit element-receiving chamber having a rear opening. The case (14) is made of a synthetic material, and a lid thereof is also made of the same material. The case and lid are integrally connected to each other at one side by an integral hinge (19) so that the lid can be opened and closed, and a sliding lock closure (6) and a hook are formed on the case (14) and the lid respectively, for keeping the lid closed on the case (14). A display lamp chamber (17) projecting from a back face of the case (14) is formed on the front side of the circuit element-receiving chamber (25) of the case (14). A green flashing light (21) indicates the heating unit is functioning normally. A red light (22) that is showing a constant red light indicates the unit is on. A red light (23) that is flashing indicates the programmed time of 100 hours use is ending within the next 60 minutes. When this occurs the unit must be returned to the factory to be reconditioned and reprogrammed for another 100 hours of use. A hanging portion (18) is formed on an upper portion of the case (14), and a band (1) is provided on the hanging portion (18). An annular hanging fixture is attached to a top end of the band (1). The length of the band (1) can optionally be adjusted by a length adjusting member so that the case (14) can be hung down at an optional position to the infusion site.

As shown in FIGS. 2, 3, 4, and 5, an inlet groove having a U-shaped section is formed on an upper edge of the front face of the case (14), and an outlet groove having a U-shaped section is formed on the front side of the warming U-shaped channels of the case (14). Temperature control thermistors (5) are attached to the U-shaped channels to slightly project from the circuit element-receiving chamber. In this embodiment, the thermistors (5) are arranged such that standard resistance corresponds to a temperature of 37°±1° C. and a temperature change is detected as a change of quantity of electricity.

Figure 4:
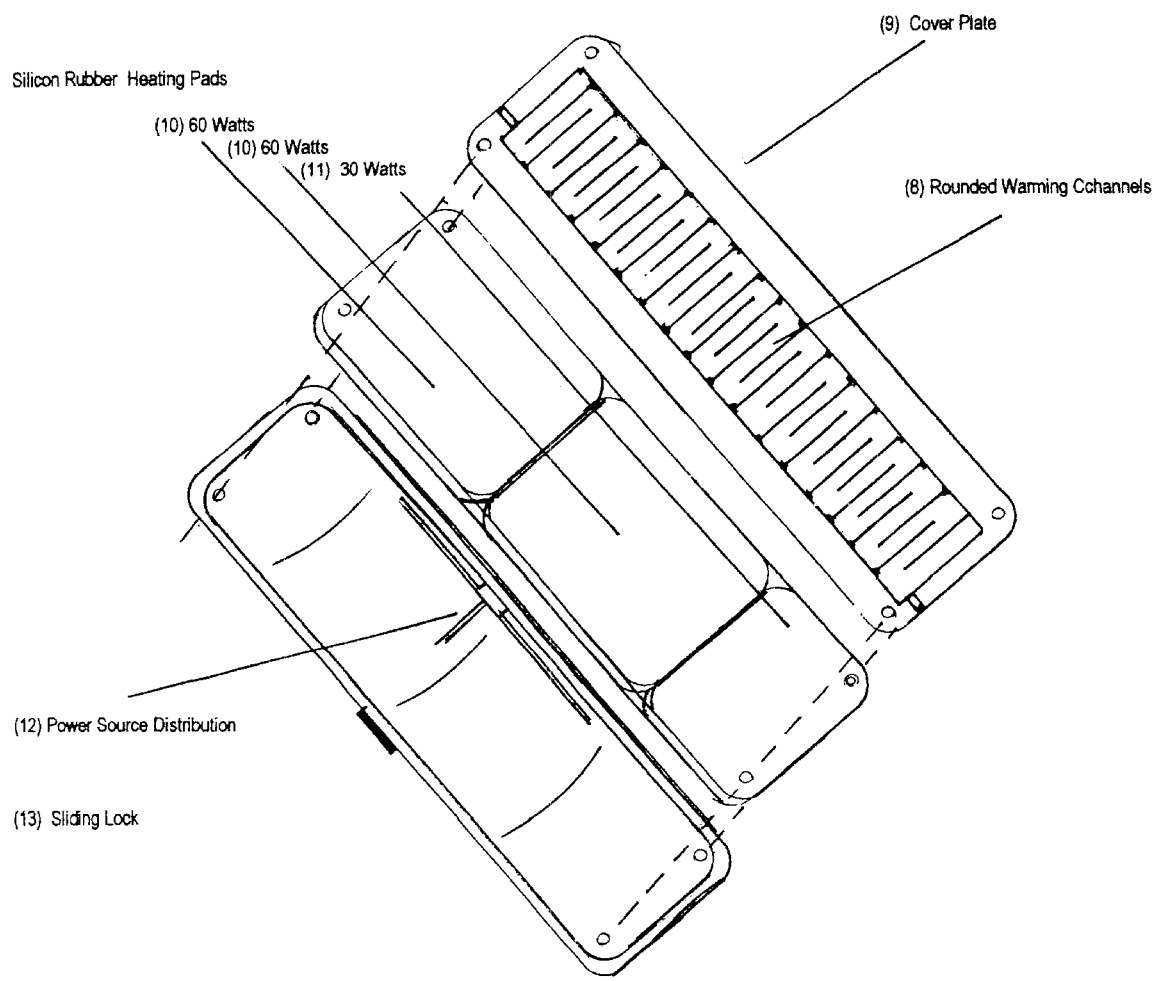
FIG. 4 is a fragmentary perspective view illustrating the manner in which the U-shaped warming channels, the heating units pads and the top cover are attached.
Figure 5:
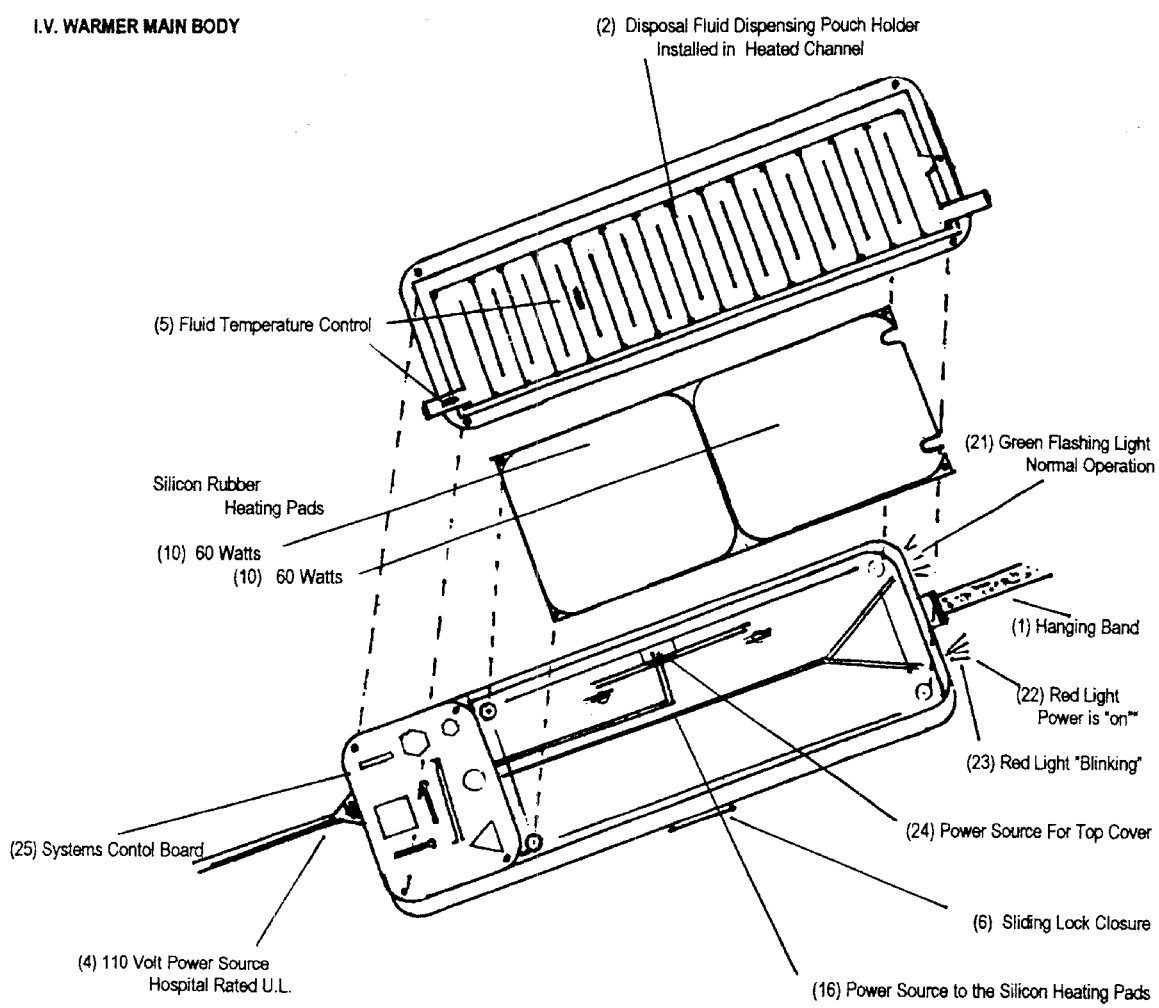
FIG. 5 is a fragmentary perspective view illustrating the manner in which the U-shaped warming channels, the heating units pad, the circuit board and the power distribution is contained in the heating device.
Figure 6:
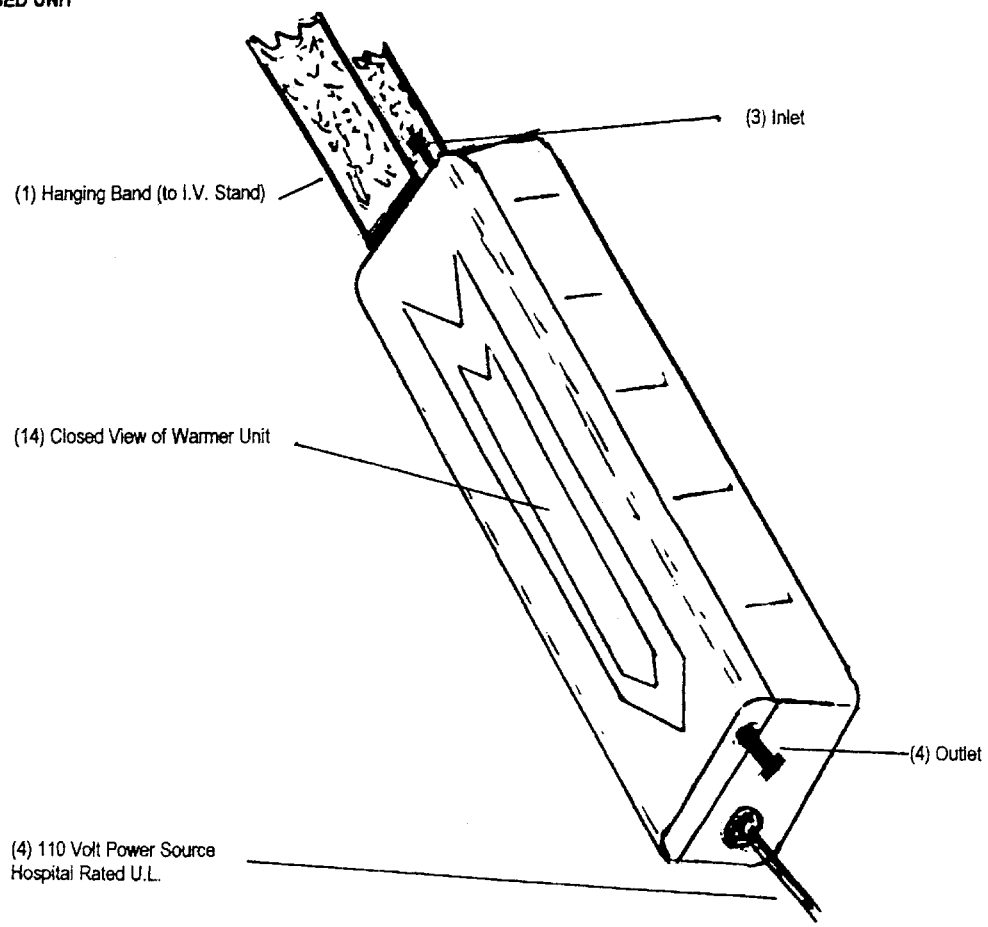
FIG. 6 is a front view of the heater. Arrow is to assist the technician and to help to insure proper installed direction of the Disposable Cellular Pouch into the warmer.

As shown in FIGS. 4 and 5, heating pads (10) or (11) are put on a heat insulating material and the heating pads (10) or (11) and the heat insulating material are fixed to the heater-receiving chambers (8) of the case (14) by means of a plurality of screws. The heater is comprised of heating pads segments (10) or (11) composed of an aluminum plate having an alumite treated surface and an electric heating pad (10) or (11) bonded to the back surface of heater segment (8) by silicone rubber, so that discharge of heat is prevented. Preferably, the electric heating pads (10) or (11) are formed of a heating wire in a layer of rubber. As shown in FIGS. 4 and 5, a holding groove having U-shaped channel sections are formed on the front surface of the heater segments, U-shaped channels extending in left and right directions from the top inlet (3) to the lower outlet (4). The Disposable Cellular Pouch (7) is slightly smaller than the outer diameter of U-shaped channels (2). Both ends of the Disposable Cellular Pouch holder (2)(8) communicate with the inlet groove (3) and outlet groove (4) of the case (14), respectively. Accordingly, the lower half of the periphery of the Disposable Cellular Pouch is intimately contacted with the Disposable Cellular Pouch Holders (2)(8), and the Disposable Fluid Dispensing Pouch is heated in the meandering U-shaped warming channels (2)(8).

As shown in FIG. 5, overheat sensing thermistors (5) for detecting change of the temperature are fixed to the back surface of the Disposable Cellular Pouch U-shaped holder (2) so that the temperature of the heating element is detected and the resistance of the thermistors (5) are drastically reduced when the temperature of the heating elements (8)(2) exceeds 41° C. Further, the overheat sensing thermistors (5) has a function of stopping the heating operation of the heating element (8)(2) by this reduction of the resistance. As shown in FIGS. 4 and 5, silicone rubber heating pads (10)(11) are embedded in a recess surrounded by the holding groove of the main body and the lid of the warmer to further diminish the thermal capacity of the heating elements (8)(2) composed of a base of aluminum. Since the thermal capacity of the heater segments are thus diminished, when the heater segments are heated at a predetermined temperature by the heating element (10)(11), overshooting owing to excessive heating of the heater proper can be prevented, and it is possible to elevate the temperature of the heater segment to the predetermined level in a very short time.

As shown in FIG. 5, control circuit elements are arranged on a printed circuit board (not shown in detail), which is situated in the circuit element-receiving chamber and is supported on the bottom of the case (14). A pilot lamp (17) is placed in the display lamp chamber, a green flashing light (21) indicates the heating unit is functioning normally. A red light (22) that is show a constant red light indicates the unit is on. A red light (23) that is flashing indicates the programmed time of 100 hours use is ending within the next 60 minutes. When this occurs the unit must be returned to the factory to be reconditioned and reprogrammed for another 100 hours of use. The 110 volt power source (4) is connected to the above-mentioned printed circuit through a bush in the lower portion of the case (14) and a plug is connected to the other end of the cord.

Figure 7:
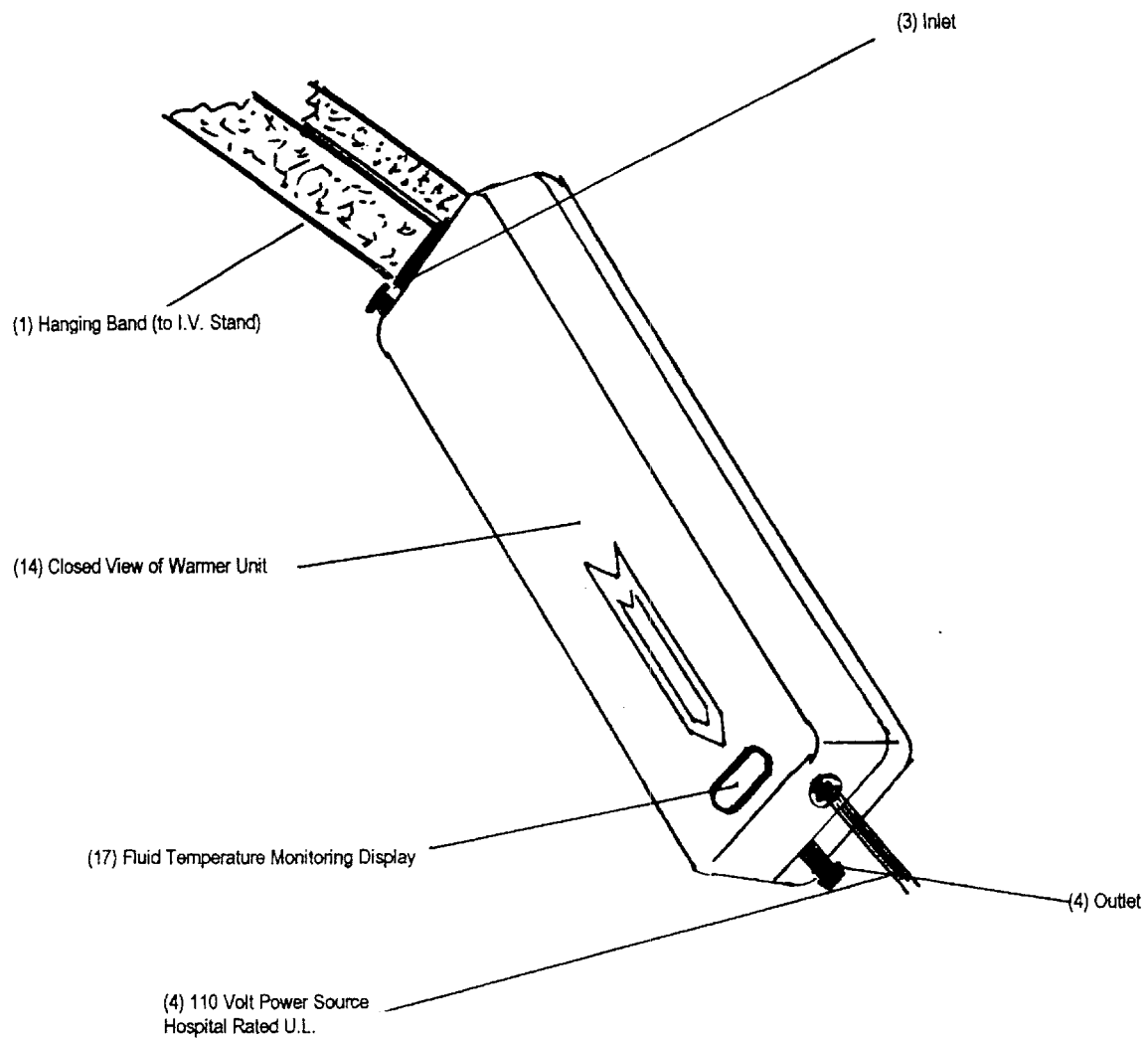
FIG. 7 is a back view of the heater. The fluid temperature monitoring display is mounted on the back of the unit to assist the Medical Technician. The unit will be facing the opposite direction with the back of the unit in their view. The Technician can read the temperature without turning the unit around to see it.

As particularly shown in FIG. 7, a window is formed on the warmer near the bottom at outlet (4), the display lamp chamber (17) of the case (14) is exposed on the back face and the light of the pilot lamp can be seen by the Medical Technician without handling or turning the unit around. In a modification of the invention the lid may have the window for the display lamp chamber (7) and be connected to the case (14) by changing the location of the control board to the lid from the main body of the warmer. In addition to the read out window, two other control lamps (21)(22) are provide. Control lamp (21) is a green flashing lamp that indicates the unit is functioning normally. Control lamp (22) is a red lamp that is showing a constant red light that indicates the unit is on. The Max One I.V. Warmer is a reusable unit that is programmed for 100 hours of use before it must be returned to the factory to be reprogrammed for another 100 hours. If the red light is flashing it is an indication the time limit on the reusable warmer is within 1 hour (60 minutes) of closing down and will not function until it is reprogrammed at the factory.

Figure 3:
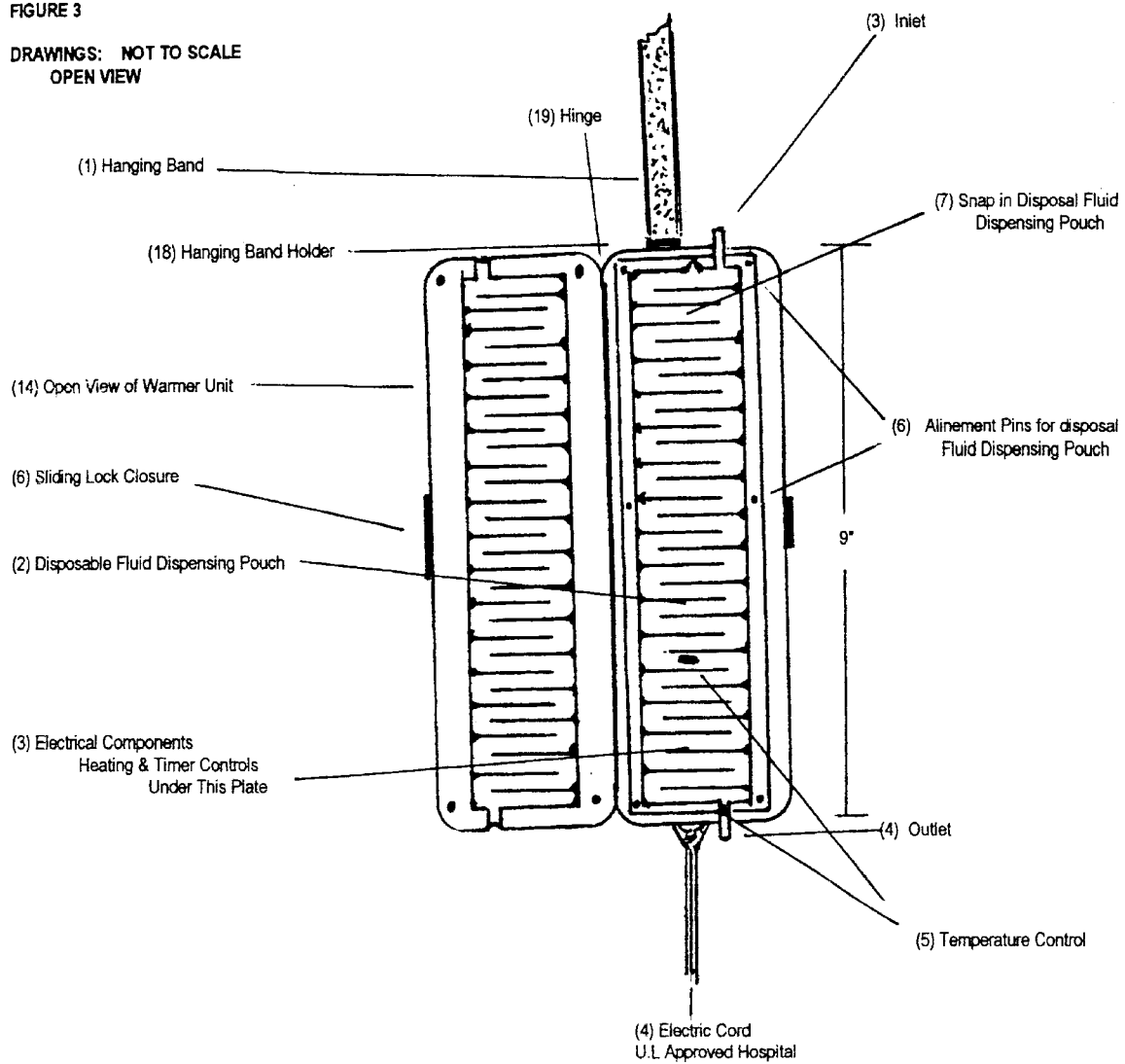
FIG. 3 is a perspective view illustrating the manner in which a Disposable Cellular Pouch is situated in the heating device and the lid is open and attached to the cover unit.

As shown in FIG. 3, the U-shaped channel plates made of aluminum are fixed to the inside of the lid (8) and the main body of the warmer (2) by means of screws to hold them in place. A heat insulating material is provided between the U-shaped channel plate (24) and the lid. Further, U-shaped channel plates presses completely over the Disposable Cellular Pouch and is completely contacted with the inner circumferential face of the U-shaped channel plates as shown in FIG. 3. Accordingly, the periphery of the Disposable Cellular Pouch is completely pressed to and contacted with the inner circumferential face of the U-shaped channel plates and therefore, wasteful discharge of heat can be prevented at the time of heating and the thermal efficiency can be increased.

The warmer (14) is hung down by the band (1) for instillation or blood transfusion. As shown in FIG. 3, the U-shaped channel plates (24) with the Disposable Cellular Pouch in place. The lid is closed and the plug is connected to the power source. At this point, the temperature of the liquid in the Disposable Cellular Pouch is lower than 5° C. so that the resistance of the temperature control thermistor (5) is maintained at a high level. Accordingly, the voltage fed into the temperature sensing circuit is higher than the standard voltage and pulses are generated to open to thereby cause the heating elements to generate heat. Thus, the Disposable Cellular Pouch is heated to warm the instillation liquid.

At the time of heating, the Disposable Cellular Pouch is intimately contacted with and pressed to the now fully rounded heating channels of the heater segment by the pressing U-shaped channel plates disposed on the inside of the lid and the main body of the warmer. Therefore, the heat of the heater segment is assuredly conducted to the Disposable Cellular Pouch without wasteful radiation of heat from the heater U-shaped channels. As a result, the thermal efficiency can be improved and uneven heating of the liquid passing through the Disposable Cellular Pouch can be prevented.

Since the Disposable Cellular Pouch is of a custom horizontally designed shape for the U-shaped channels and generally the case (14) is situated vertically, the instillation liquid is stored in the horizontal liquid tubes and is heated therein. Also by virtue of this feature, uneven heating of the instillation liquid can be prevented. Further, since the horizontal tubes in the Disposable Cellular Pouch is a custom shape, the contact area between the Disposable Cellular Pouch and the heat in the rounded heating channels is increased and the time for passing the liquid through the rounded heating channels is prolonged. Accordingly, uneven heating of the liquid can be prevented completely.

As the instillation liquid is heated, the resistance value of the temperature control thermistor (5) is gradually lowered, and when the temperature of the liquid in the Disposable Cellular Pouch is elevated to 37° C., the voltage fed into the temperature sensing circuit (5) becomes equal to the standard voltage. At this point, generation of pulses is stopped. Accordingly, the power source is then kept in the "off" state to stop generation of heat by the heating element, whereby further rise of the temperature of the instillation liquid is prevented. When the temperature is lowered again below 35° C. after a certain time is elapsed, the above mentioned operation is repeated. Therefore, the temperature of the instillation liquid is always maintained at a certain level (37° C.) and at this temperature, instillation is carried out.

When a large quantity of the instillation liquid flows through the liquid feed pipe, heating is carried out in the same manner as described above. However because of a large amount of flow, the thermistor (5) shows a resistance value corresponding to a temperature lower than 35° C. and abnormal heat generation takes place in the heating channels. This dangerous phenomenon is prevented in the present invention by the following operation.

If the heating elements (10)(11) are continuously heated to thereby reach about 63° C., the resistance of the overheat sensing thermistors (5) are abruptly lowered from a high value to a very low value. Since this resistance value is much lower than the resistance value of the thermistor (5), and electric current flows through the overheat sensing thermistor (5), whereby the voltage fed into the temperature sensing circuit is lowered below the standard voltage and generation of pulses is stopped. As a result, generation of heat in the heating element (5) is stopped and overheat of the liquid beyond 63° C. can be prevented. Accordingly, even if a large quantity of the instillation liquid flows through the Disposable Cellular Pouch, instillation can be performed very safely.

As will be apparent from the forgoing illustration, the heating device of the present invention has a very small size not to occupy a large space. Further, the heating device of the present invention can be handled and transferred very easily, and there can be attained an advantage that the operation efficiency of instillation such as dripping or blood/blood products transfusion can be remarkably improved. Since a Disposable Cellular Pouch is being incorporated in the procedure, the Disposable Cellular Pouch is designed in different milliliter size tub configurations to fit the procedure no matter what the procedure may be, from Pre-Born to Children to all Adult instillation procedures.

The present invention has been described in lay terms with reference to most preferred embodiments. It is apparent that certain changes and modifications will be made without departing from the spirit and scope of the present invention. It is intended that all matter contained in the above description or shown in the accompanying drawing shall be interpreted as illustrative and not in a limiting sense as would be prepared by a professional Patent Attorney with the help of a professional draftsman.

What is claimed is:

1. A heating device for instillation comprising a casing having hanging means at one end thereof for vertically supporting the casing during use of the device, said casing including a circuit element receiving chamber and a heater receiving chamber having a front opening for securing the Disposable Cellular Pouch, a lid for at least covering said front opening of the heater receiving chamber, a heater situated in said heater receiving chamber, said heater including a heater segment coextensive with, disposed in and filling said front opening and an electric heating element attached to a backside and front side of the heater segment for heating the segment, said heater segment having U-shaped channels on a front and backside thereof for receiving a Disposable Cellular Pouch therein a liquid through which an instillation liquid to be heated flows, said lid being arranged to cover said U-shaped channels and feed pipe received therein when in closed position, said groove having left and right curves and extending from an upper portion of the heater segment to a lower portion thereof to keep the instillation liquid in the liquid feed of the disposable Cellular Pouch between left and right curves for a period sufficient to heat the liquid, and electric circuit means situated in said circuit element receiving chamber, said electric circuit means including first and second temperature control thermistors, the first thermistor sensing temperature of the instillation liquid after passing through the length of the heater segment groove for operating said circuit means to intermittently energize the heating element to heat to instillation liquid flowing through the disposable tubular holder/channels to a predetermined temperature, the second thermistor being provided at the electric heating element for operating said circuit means to turn off the electric circuit means when the electrical heating element is heated beyond a predetermined temperature due to excess flow of the instillation liquid to thereby override the control of the heating element by the first thermistor such that instillation fluid flow is not halted and will continue to flow without the heating, wherein the electric circuit means further comprises a programmable control unit, adapted to shut down the heating device after it has been in use for a predetermined period and to provide alarm while approaching the predetermined period.

2. A heating device for instillation according to claim 1, in which said lid includes a heating device with U-shaped channels pressing member to intimately hold a Disposable Cellular Pouch in the groove when the lid is closed, insulating materials being provided between the lid and the pressing member and between the casing and the electric heating element.

3. A heating device for instillation according to claim 1, in which the casing and lid are integrally formed of a synthetic resin and are joined by an integral hinge portion so that the lid can be freely opened and closed, and a sliding anchoring projection and a hook are provided on the casing and the lid respectively to keep the lid closed.

* * * * *